United States Patent

Bergmann et al.

(10) Patent No.: US 8,367,788 B2
(45) Date of Patent: Feb. 5, 2013

(54) CATALYTIC PROCESS FOR PREPARING (METH)ACRYLIC ESTERS OF N-HYDROXYALKYLATED LACTAMS

(75) Inventors: Hermann Bergmann, Singapore (SG); Frank Hoefer, Bad Duerkheim (DE); Maximilian Angel, Schifferstadt (DE)

(73) Assignee: BASF SE, Ludwigshafen (DE)

( * ) Notice: Subject to any disclaimer, the term of this patent is extended or adjusted under 35 U.S.C. 154(b) by 609 days.

(21) Appl. No.: 12/524,587

(22) PCT Filed: Feb. 11, 2008

(86) PCT No.: PCT/EP2008/051586
§ 371 (c)(1),
(2), (4) Date: Jul. 27, 2009

(87) PCT Pub. No.: WO2008/098887
PCT Pub. Date: Aug. 21, 2008

(65) Prior Publication Data
US 2010/0113725 A1    May 6, 2010

(30) Foreign Application Priority Data

Feb. 15, 2007   (EP) .................................... 07102484

(51) Int. Cl.
*C08F 26/08*   (2006.01)

(52) U.S. Cl. .......... 526/264; 526/89; 526/212; 526/216; 526/221

(58) Field of Classification Search ............... 526/89, 526/221, 264, 212, 216
See application file for complete search history.

(56) References Cited

U.S. PATENT DOCUMENTS

| 2,882,262 A * | 4/1959 | Smith et al. .................. 526/264 |
| 2003/0113365 A1 | 6/2003 | Schaberg et al. |
| 2006/0036063 A1 | 2/2006 | Hofer et al. |
| 2007/0123673 A1 | 5/2007 | Hofer et al. |

FOREIGN PATENT DOCUMENTS

| DE | 1 595 233 | 10/1969 |
| GB | 930 668 | 7/1963 |
| WO | 03 006568 | 1/2003 |
| WO | 2006 012980 | 2/2006 |

OTHER PUBLICATIONS

U.S. Appl. No. 12/525,826, filed Aug. 5, 2009, Bergmann et al.
U.S. Appl. No. 12/525,686, filed Aug. 4, 2009, Bergmann et al.
U.S. Appl. No. 12/597,175, filed Oct. 23, 2009, Brockmeyer et al.

* cited by examiner

*Primary Examiner* — David W Wu
*Assistant Examiner* — Marie Reddick
(74) *Attorney, Agent, or Firm* — Oblon, Spivak, McClelland, Maier & Neustadt, L.L.P.

(57) ABSTRACT

A process for catalytically preparing (meth)acrylic esters of N-hydroxyalkylated lactams and to the use thereof.

11 Claims, No Drawings

CATALYTIC PROCESS FOR PREPARING (METH)ACRYLIC ESTERS OF N-HYDROXYALKYLATED LACTAMS

The present invention relates to a process for catalytically preparing (meth)acrylic esters of N-hydroxyalkylated lactams and to the use thereof.

In the context of the present invention, (meth)acrylic acid is understood to mean acrylic acid and/or methacrylic acid, and (meth)acrylic esters are understood to mean acrylic esters and/or methacrylic esters.

(Meth)acrylic esters are prepared usually by catalytically esterifying (meth)acrylic acid or transesterifying other (meth) acrylic esters with alcohols. Strong acids or bases are frequently used, so that acid- or base-sensitive (meth)acrylic esters generally cannot be prepared in a controlled manner by an esterification or transesterification in this way.

(Meth)acrylic esters of N-hydroxyalkylated lactams are known.

WO 03/006568 A1 describes the acidic esterification of acrylic acid with hydroxyethylpyrrolidone using p-toluenesulfonic acid as a catalyst. The yield is, however, only 71%.

German application DE 10 2005 052 931.3, which was yet to be published at the priority date of the present application, discloses a catalytic process for preparing (meth)acrylic esters of N-hydroxyalkylated lactams, in which the esterification or transesterification is performed in the presence of a heterogeneous inorganic salt.

DE 1 595 233 and GB 930 668 disclose the transesterification of N-hydroxyalkyl-lactams with (meth)acrylic esters in the presence of alkali metal alkoxides and ammonium alkoxides, and also titanium tetraalkoxides. A disadvantage of these processes is that the traces of the catalysts remaining in the product influence any polymerization which follows, and therefore have to be removed from the product in a complicated manner. Such a removal is usually performed by means of aqueous scrubbing, so that the product subsequently has to be dried.

GB 930 668 likewise describes the preparation of (meth) acrylic esters of N-hydroxyalkylated lactams by reacting N-hydroxyalkyllactams with (meth)acryloyl chloride. However, the use of (meth)acryloyl chloride in the reactions described leads to salt formation and, owing to its high reactivity, to unselective reactions, for example Michael additions.

It was therefore an object of the present invention to provide an alternative process with which (meth)acrylic esters of N-hydroxyalkylated lactams can be prepared in high conversions and high purities from simple reactants. The synthesis should proceed under mild conditions, so that the resulting products have a low color number and high purity. In particular, the process should be performable industrially.

The object is achieved by a process for preparing (meth) acrylic esters (F) of N-hydroxyalkylated lactams, in which cyclic N-hydroxyalkylated lactams (L)

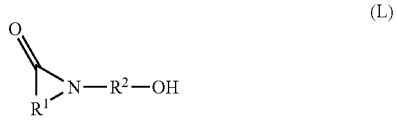

(L)

in which
$R^1$ is $C_1$-$C_5$-alkylene, or $C_2$-$C_{20}$-alkylene interrupted by one or more oxygen and/or sulfur atoms and/or one or more substituted or unsubstituted imino groups and/or by one or more cycloalkyl, —(CO)—, —O(CO)O—, —(NH)(CO) O—, —O(CO)(NH)—, —O(CO)— or —(CO)O— groups, where the radicals mentioned may each be substituted by aryl, alkyl, aryloxy, alkyloxy, heteroatoms and/or heterocycles,
with the proviso that $R^1$ must not have any atom other than a carbon atom directly adjacent to the lactam carbonyl group,
$R^2$ is $C_1$-$C_{20}$-alkylene, $C_5$-$C_{12}$-cycloalkylene, $C_6$-$C_{12}$-arylene, or $C_2$-$C_{20}$-alkylene interrupted by one or more oxygen and/or sulfur atoms and/or one or more substituted or unsubstituted imino groups and/or by one or more cycloalkyl, —(CO)—, —O(CO)O—, —(NH)(CO)O—, —O(CO) (NH)—, —O(CO)— or —(CO)O— groups, where the radicals mentioned may each be substituted by aryl, alkyl, aryloxy, alkyloxy, heteroatoms and/or heterocycles, or
$R^2$—OH is a group of the formula —$[X_i]_k$—H,
k is from 1 to 50 and
$X_i$, for each $i$=1 to k, may each independently be selected from the group of —$CH_2$—$CH_2$—O—, —$CH_2$—$CH_2$—N(H)—, —$CH_2$—$CH_2$—$CH_2$—N(H)—, —$CH_2$—CH(NH_2)—, —$CH_2$—CH(NHCHO)—, —$CH_2$—CH($CH_3$)—O—, —CH($CH_3$)—$CH_2$—O—, —$CH_2$—C($CH_3$)_2—O—, —C($CH_3$)_2—$CH_2$—O—, —$CH_2$—$CH_2$—$CH_2$—O—, —$CH_2$—$CH_2$—$CH_2$—$CH_2$—O—, —$CH_2$—CHVin-O—, —CHVin-$CH_2$—O—, —$CH_2$—CHPh-O— and CHPh-$CH_2$—O—, in which Ph is phenyl and Vin is vinyl,
in the presence of at least one catalyst (K) selected from the group consisting of alkali metal hydroxides, alkaline earth metal hydroxides and metal acetylacetonates, is esterified with (meth)acrylic acid (S) or transesterified with at least one (meth)acrylic ester (D).

Hereinafter, the reactants (meth)acrylic acid (S) and (meth) acrylic ester (D) are also summarized together under the term (meth)acrylic compound (B).

With the aid of the process according to the invention, the preparation of (meth)acrylates of N-hydroxyalkylated lactams is possible with at least one of the following advantages:
high yield,
mild reaction conditions,
good color numbers and
no washing steps required to purify the reaction mixture.

In the above definitions,
$C_1$-$C_{20}$-alkylene optionally substituted by aryl, alkyl, aryloxy, alkyloxy, heteroatoms and/or heterocycles is, for example, methylene, 1,2-ethylene, 1,2-propylene, 1,3-propylene, 1,4-butylene, 1,6-hexylene, 2-methyl-1,3-propylene, 2-ethyl-1,3-propylene, 2,2-dimethyl-1,3-propylene, 2,2-dimethyl-1,4-butylene,
$C_5$-$C_{12}$-cycloalkylene optionally substituted by aryl, alkyl, aryloxy, alkyloxy, heteroatoms and/or heterocycles is, for example, cyclopropylene, cyclopentylene, cyclohexylene, cyclooctylene, cyclododecylene,
$C_1$-$C_{20}$-alkylene optionally substituted by aryl, alkyl, aryloxy, alkyloxy, heteroatoms and/or heterocycles and interrupted by one or more oxygen and/or sulfur atoms and/or one or more substituted or unsubstituted imino groups and/or by one or more cycloalkyl, —(CO)—, —O(CO)O—, —(NH) (CO)O—, —O(CO)(NH)—, —O(CO)— or —(CO)O— groups is, for example, 1-oxa-1,3-propylene, 1,4-dioxa-1,6-hexylene, 1,4,7-trioxa-1,9-nonylene, 1-oxa-1,4-butylene, 1,5-dioxa-1,8-octylene, 1-oxa-1,5-pentylene, 1-oxa-1,7-heptylene, 1,6-dioxa-1,10-decylene, 1-oxa-3-methyl-1,3-propylene, 1-oxa-3-methyl-1,4-butylene, 1-oxa-3,3-dimethyl-1,4-butylene, 1-oxa-3,3-dimethyl-1,5-pentylene, 1,4-dioxa-3,6-dimethyl-1,6-hexylene, 1-oxa-2-methyl-1,3-propylene, 1,4-dioxa-2,5-dimethyl-1,6-hexylene, 1-oxa-1,5-pent-3- enylene, 1-oxa-1,5-pent-3-ynylene, 1,1-, 1,2-, 1,3- or 1,4-cyclohexylene, 1,2- or 1,3-cyclopentylene, 1,2-, 1,3- or 1,4-phenylene, 4,4'-biphenylene, 1,4-diaza-1,4-butylene, 1-aza-1,3-propylene, 1,4,7-triaza-1,7-heptylene, 1,4-diaza-1,6-hexylene, 1,4-diaza-7-oxa-1,7-heptylene, 4,7-diaza-1-oxa-1, 7-heptylene, 4-aza-1-oxa-1,6-hexylene, 1-aza-4-oxa-1,4-butylene, 1-aza-1,3-propylene, 4-aza-1-oxa-1,4-butylene, 4-aza-1,7-dioxa-1,7-heptylene, 4-aza-1-oxa-4-methyl-1,6-hexylene, 4-aza-1,7-dioxa-4-methyl-1,7-heptylene, 4-aza-1, 7-dioxa-4-(2'-hydroxyethyl)-1,7-heptylene, 4-aza-1-oxa-(2'-hydroxyethyl)-1,6-hexylen or 1,4-piperazinylene and $C_6$-$C_{12}$-arylene optionally substituted by aryl, alkyl, aryloxy, alkyloxy, heteroatoms and/or heterocycles is, for example, 1,2-, 1,3- or 1,4-phenylene, 4,4'-biphenylene, tolylene or xylylene.

Examples of $R^1$ are 1,2-ethylene, 1,2-propylene, 1,1-dimethyl-1,2-ethylene, 1-hydroxymethyl-1,2-ethylene, 2-hydroxy-1,3-propylene, 1,3-propylene, 1,4-butylene, 1,5-pentylene, 2-methyl-1,3-propylene, 2-ethyl-1,3-propylene, 2,2-dimethyl-1,3-propylene and 2,2-dimethyl-1,4-butylene; preference is given to 1,4-butylene, 1,5-pentylene and 1,3-propylene, particular preference to 1,3-propylene.

Examples of $R^2$ are 1,2-ethylene, 1,2-propylene, 1,1-dimethyl-1,2-ethylene, 1-hydroxymethyl-1,2-ethylene, 2-hydroxy-1,3-propylene, 1,3-propylene, 1,4-butylene, 1,6-hexylene, 2-methyl-1,3-propylene, 2-ethyl-1,3-propylene, 2,2-dimethyl-1,3-propylene and 2,2-dimethyl-1,4-butylene, 1,2-cyclopentylene, 1,3-cyclopentylene, 1,2-cyclohexylene, 1,3-cyclohexylene, ortho-phenylene, 3-oxa-1,5-pentylene, 3,6-dioxa-1,8-octylene and 3,6,8-trioxa-1,8,11-undecylene; preference is given to 1,2-ethylene, 1,2-propylene, 1,3-propylene, particular preference to 1,2-ethylene and 1,2-propylene, and very particular preference to 1,2-ethylene.

Preferred species (L) are N-(2-hydroxyethyl)pyrrolidone, N-(2-hydroxypropyl)pyrrolidone, N-(2'-(2-hydroxyethoxy) ethyl)pyrrolidone, N-(2-hydroxyethyl)caprolactam, N-(2-hydroxypropyl)caprolactam and N-(2'-(2-hydroxyethoxy) ethyl)caprolactam; preference is given to N-(2-hydroxyethyl) pyrrolidone and N-(2-hydroxypropyl)pyrrolidone, particular preference to N-(2-hydroxyethyl)pyrrolidone.

When the N-hydroxylated lactams (L) are optically active, they are preferably used in racemic form or as a diastereomer mixture, but it is also possible to use them as pure enantiomers or diastereomers or as enantiomer mixtures.

In the reaction step, the esterification with (meth)acrylic acid (S) or preferably the transesterification with at least one, preferably exactly one, (meth)acrylic ester (D) is, in accordance with the invention, effected in the presence of at least one catalyst (K) selected from the group consisting of alkali metal hydroxides, alkaline earth metal hydroxides and metal acetylacetonates.

(Meth)acrylic acid (S) may be for the esterification or (meth)acrylic esters (D) of a saturated alcohol may be for the transesterification, preferably saturated $C_1$-$C_{10}$-alkyl esters or $C_3$-$C_{12}$-cycloalkyl esters of (meth)acrylic acid, more preferably saturated $C_1$-$C_4$-alkyl esters of (meth)acrylic acid.

In the context of this document, saturated means compounds without C—C multiple bonds (except of course the C═C double bond in the (meth)acryloyl units).

Examples of compounds (D) are methyl (meth)acrylate, ethyl (meth)acrylate, n-butyl (meth)acrylate, isobutyl (meth) acrylate, tert-butyl (meth)acrylate, n-octyl (meth)acrylate and 2-ethylhexyl (meth)acrylate, 1,2-ethylene glycol di- and mono(meth)acrylate, 1,4-butanediol di- and mono(meth) acrylate, 1,6-hexanediol di- and mono(meth)acrylate, trimethylolpropane tri(meth)acrylate and pentaerythritol tetra (meth)acrylate.

Particular preference is given to methyl (meth)acrylate, ethyl (meth)acrylate, n-butyl (meth)acrylate and 2-ethylhexyl (meth)acrylate, very particular preference to methyl (meth) acrylate, ethyl (meth)acrylate and n-butyl (meth)acrylate, in particular methyl (meth)acrylate and ethyl (meth)acrylate and especially methyl (meth)acrylate.

Catalysts (K) usable in accordance with the invention are selected from the group consisting of alkali metal hydroxides, alkaline earth metal hydroxides and metal acetylacetonates.

These catalysts may be either homogeneous or heterogeneous. In the context of this document, heterogeneous catalysts are, in accordance with the invention, those which have a solubility in the reaction medium at 25° C. of not more than 1 g/l, preferably of not more than 0.5 g/l and more preferably of not more than 0.25 g/l.

In the context of the present application, alkali metal and alkaline earth metal hydroxides are understood to mean basic compounds which have a $pK_B$ of not more than 7.0, preferably not more than 6.0 and more preferably not more than 4.0.

The alkali metal and alkaline earth metal hyxdroxides may be used either in solid form or in the form of solutions, for example as aqueous solutions. Preference is given to adding the alkali metal and alkaline earth metal hydroxides to the process according to the invention in solid form.

Suitable alkali metal hydroxides are, for example, lithium hydroxide, sodium hydroxide and potassium hydroxide. Suitable alkaline earth metal hydroxides are, for example, magnesium hydroxide and calcium hydroxide. Preference is given to alkali metal hydroxides such as lithium hydroxide, sodium hydroxide and potassium hydroxide.

Catalysts (K) which are likewise suitable are metal acetylacetonates. Metal acetylacetonates are metal chelates with the enolate anion of 2,4-pentanedione (acetylacetone) and have the general formula $M_n(C_5H_7O_2)_n$ or $M_n(acac)_n$. Useful metals M include numerous metals, especially transition metals. Preference is given to metals M selected from the group of the transition metals, alkali metals, alkaline earth metals and aluminum. Suitable alkali metals and alkaline earth metals are, for example, lithium, sodium, potassium, magnesium and calcium. Preference is given to using aluminum, lithium, sodium, potassium and calcium. The transition metals used are preferably titanium, zirconium, chromium, manganese, cobalt, nickel and copper. Preferred representatives of this group are lithium acetylacetonate (Li(acac)), sodium acetylacetonate (Na(acac)) and potassium acetylacetonate (K(acac)), and also calcium acetylacetonate ($Ca(acac)_2$).

The esterification or transesterification catalyzed by the catalyst (K) is effected generally at from 30 to 140° C., preferably at from 30 to 100° C., more preferably at from 40 to 90° C. and most preferably at from 50 to 80° C.

In a preferred embodiment of the process according to the invention, the reaction is performed under gentle vacuum of, for example, from 200 hPa to standard pressure, preferably from 200 to 600 hPa and more preferably from 300 to 500 hPa when the water released in the esterification or the low-boiling alcohol formed in the transesterification is to be distilled off, if appropriate as an azeotrope.

The molar ratio between (meth)acrylic acid (S) or (meth) acrylic ester (D) and N-hydroxyalkylated lactam (L) is, in the case of the esterification or transesterification catalyzed by a catalyst (K), generally 1-6:1 mol/mol, preferably 1-5:1 mol/mol and more preferably 1-4:1 mol/mol.

The reaction time in the esterification or transesterification catalyzed by a catalyst (K) is generally from 45 min to 18 hours, preferably from 2 hours to 12 hours and more preferably from 3 to 10 hours.

The content of catalyst (K), which is selected from the group of the alkali metal hydroxides, alkaline earth metal hydroxides and metal acetylacetonates, in the reaction medium is generally in the range from about 0.01 to 5 mol %, preferably 0.1-3 mol % and more preferably 0.3-2 mol %, based on the sum of the N-hydroxyalkylated lactams (L) used.

In the esterification or transesterification, polymerization inhibitors (as described below) are absolutely necessary.

The presence of oxygen as gases (see below) during the reaction catalyzed by a catalyst (K) is preferred.

In a preferred embodiment of the process according to the invention, an oxygenous gas is therefore introduced continuously into the reaction mixture during the reaction. In the case of further workup of the crude product, for example by distillation or rectification, preference is likewise given to continuous oxygen introduction.

In the inventive esterification or transesterification, the products are generally obtained with a color number below 500 APHA, preferably below 200 APHA and more preferably below 150 APHA (to DIN ISO 6271).

The reaction can proceed in organic solvents or mixtures thereof or without addition of solvents. The mixtures are generally substantially anhydrous i.e. the water content is below 10% by weight, preferably below 5% by weight, more preferably below 1% by weight and most preferably below 0.5% by weight. Generally the water content is in a range from 100 to 5000 ppm, preferably 500 to 1000 ppm. Moreover, the mixtures are substantially free of primary and secondary alcohols, i.e. alcohol content below 10% by weight, preferably below 5% by weight, more preferably below 1% by weight and most preferably below 0.5% by weight.

Suitable organic solvents are those known for these purposes, for example tertiary monools such as $C_3$-$C_6$-alcohols, preferably tert-butanol, tert-amyl alcohol, pyridine, poly-$C_1$-$C_4$-alkylene glycol di-$C_1$-$C_4$-alkyl ethers, preferably polyethylene glycol di-$C_1$-$C_4$-alkyl ethers, for example 1,2-dimethoxyethane, diethylene glycol dimethyl ether, polyethylene glycol dimethyl ether 500, $C_1$-$C_4$-alkylene carbonates, especially propylene carbonate, $C_3$-$C_6$-alkyl acetates, especially tert-butyl acetate, THF, toluene, 1,3-dioxolane, acetone, isobutyl methyl ketone, ethyl methyl ketone, 1,4-dioxane, tert-butyl methyl ether, cyclohexane, methylcyclohexane, toluene, hexane, dimethoxymethane, 1,1-dimethoxyethane, acetonitrile, and mono- or polyphasic mixtures thereof.

In a particularly preferred embodiment of the transesterification, the reaction is performed in the (meth)acrylic ester (D) used as the reactant. Very particular preference is given to performing the reaction in such a manner that the product (F), after the reaction has ended, is obtained as an about 10-80% by weight solution in the (meth)acrylic ester (D) used as the reactant, especially as a from 20 to 50% by weight solution.

The reactants are present in dissolved form, suspended as solids or in an emulsion in the reaction medium. In a preferred embodiment of the process according to the invention, the catalyst (K), which is selected from the group of the alkali metal hydroxides, alkaline earth metal hydroxides and metal acetylacetonates, is used in the absence of solvents and preferably as a solid.

The reaction can be effected continuously, for example in a tubular reactor or in a stirred reactor battery, or batchwise. In a preferred embodiment of the process according to the invention, however, all reactants, and also stabilizers and the catalyst (K) are added completely at the start of the reaction, i.e. not continuously during the course of the reaction.

The reaction can be performed in all reactors suitable for such a reaction. Such reactors are known to those skilled in the art. Preference is given to effecting the reaction in a stirred tank reactor or a fixed bed reactor.

To mix the reaction mixture, any methods may be used. Specific stirrer apparatus is not required. The mixing can be effected, for example, by injecting a gas, preferably an oxygenous gas (see below). The reaction medium may be mono- or polyphasic, and the reactants are dissolved, suspended or emulsified therein. The temperature is adjusted to the desired value during the reaction and can, if desired, be increased or reduced during the course of the reaction.

The removal of water in the case of an esterification, or alcohols which are released from the (meth)acrylic esters (D) in a transesterification, is effected continuously or stepwise in a manner known per se, for example by means of reduced pressure, azeotropic removal, stripping, absorption, pervaporation and diffusion through membranes, or extraction.

Advantageously, the esterification or transesterification is performed in the presence of an oxygenous gas, preferably air or air-nitrogen mixtures.

This stripping can be effected, for example, by passing an oxygenous gas, preferably air or an air-nitrogen mixture, through the reaction mixture, if appropriate in addition to a distillation. As already described above, in a preferred embodiment of the process according to the invention, an oxygenous gas is introduced continuously into the reaction mixture.

Suitable media for the absorption are preferably molecular sieves or zeolites (pore size, for example, in the range of about 3-10 angstrom), a removal by distillation or with the aid of suitable semipermeable membranes.

However, it is also possible to feed the mixture of (meth)acrylic esters (D) and its parent alcohol, which frequently forms an azeotrope, directly into a plant for preparing the (meth)acrylic esters (D) in order to reutilize it there in an esterification with (meth)acrylic acid.

After the reaction has ended, the reaction mixture obtained from the esterification or transesterification can be used without further purification or it can, if required, be purified in a further step.

In general, in the workup step, only the catalyst (K) used is removed from the reaction mixture, and the reaction product is removed from any organic solvent used.

A removal from the catalyst (K) is effected generally by filtration, electrofiltration, absorption, centrifugation or decantation, or by distillation or rectification. The catalyst (K) removed can subsequently be used for further reactions.

The removal from the organic solvent is effected generally by distillation, rectification or, in the case of solid reaction products, by filtration.

In the purification step, however, preference is given to removing only the catalyst (K) and any solvent used.

The reaction mixture which has been purified if appropriate is preferably subjected to a distillation in which the (meth)acrylic ester (F) of the N-hydroxyalkylated lactams is separated by distillation from unconverted (meth)acrylic acid (S) or unconverted (meth)acrylic ester (D) and any by-products formed. As already described above, in a workup of the crude product by distillation or rectification, preference is likewise given to continuous oxygen introduction.

The distillation units are usually rectification columns of customary design with a circulation evaporator and condenser. The feed is preferably into the bottom region; the bottom temperature here is, for example, 130-160° C., preferably 150-160° C., the top temperature is preferably 140-145° C. and the top pressure is 3-20 mbar, preferably from 3 to 5 mbar. It will be appreciated that the person skilled in the art can also determine other temperature and pressure ranges in which the particular (meth)acrylic esters (F) of the N-hydroxyalkylated lactams can be purified by distillation. What is essential is a separation of the desired product from reactants and by-products under conditions under which the desired product is exposed to a minimum level of degradation reaction.

The distillation unit has generally from 5 to 50 theoretical plates.

The distillation units are of a design known per se and have the customary internals. Useful column internals include in principle all common internals, for example trays, structured packings and/or random packings. Among the trays, preference is given to bubble-cap trays, sieve trays, valve trays, Thormann trays and/or dual-flow trays; among the random packings, preference is given to those comprising rings, helices, saddles, Raschig, Intos or Pall rings, Barrel or Intalox saddles, Top-Pak, etc., or braids.

Preference is given to distilling the desired product batchwise, which initially removes low boilers from the reaction mixture, usually solvent or unconverted (meth)acrylic acid (S) or (meth)acrylic ester (D). After these low boilers have been removed, the distillation temperature is increased and/or the vacuum is reduced, and the desired product is distilled off.

The remaining distillation residue is usually discarded.

The reaction conditions in the inventive esterification or transesterification are mild. Owing to the low temperatures and otherwise mild conditions, the formation of by-products which can otherwise stem, for example, from strongly acidic or basic catalysts or by undesired free-radical polymerization of the (meth)acrylic compound (B) used, which can otherwise be prevented only by adding stabilizers, in the reaction is prevented.

In the inventive reaction, additional stabilizer may be added to the reaction mixture over and above the storage stabilizer present in the (meth)acrylic compound (B) in any case, for example hydroquinone monomethyl ether, phenothiazine, phenols, for example 2-tert-butyl-4-methylphenol, 6-tert-butyl-2,4-dimethylphenol, or N-oxyls such as 4-hydroxy-2,2,6,6-tetramethylpiperidine N-oxyl, 4-oxo-2,2,6,6-tetramethylpiperidine N-oxyl or Uvinul® 4040P from BASF Aktiengesellschaft, or amines such as Kerobit® BPD from BASF Aktiengesellschaft (N,N'-di-sec-butyl-p-phenylenediamine), for example in amounts of from 50 to 2000 ppm.

The catalysts (K) used in accordance with the invention exhibit merely a low tendency to side reactions.

Furthermore, the reaction is very selective under the inventive reaction conditions; generally less than 10%, preferably less than 5%, of by-products are found (based on the conversion).

The (meth)acrylic esters (F) of N-hydroxyalkylated lactams prepared in accordance with the invention find use, for example, as monomers and comonomers in the preparation of dispersions, for example acrylic dispersions, as reactive diluents, for example in radiation-curable coating compositions or in paints, preferably in exterior paints, and also in dispersions for use in the paper sector.

The examples which follow are intended to illustrate the properties of the invention but without restricting it.

EXAMPLES

All "parts" in this document, unless stated otherwise, are understood to mean "parts by weight".

Example 1

Preparation of N-(2-hydroxyethyl)pyrrolidone methacrylate with lithium hydroxide as the catalyst with subsequent purifying distillation

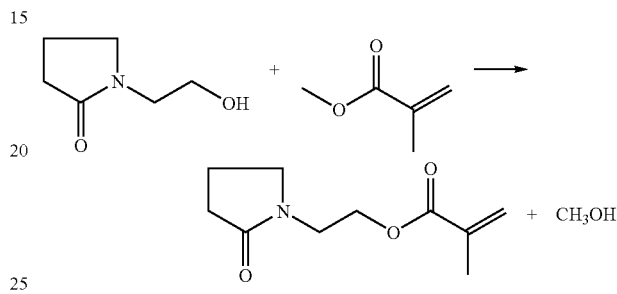

The transesterification was effected in a 750 ml Miniplant reactor with an Oldershaw column and liquid distributor. The reflux ratio was 25:1 (reflux:efflux), the stirrer speed (Anker stirrer) 400 rpm and the air introduction 1.5 l/h.

This apparatus was initially charged with 280 mg of hydroquinone monomethyl ether (350 ppm), 40 mg of phenothiazine (50 ppm), 600 g (6.0 mol) of methyl methacrylate (MMA) and 194 g (1.5 mol) of hydroxyethylpyrrolidone, which were stirred. Subsequently, 0.72 g (30 mmol; 2.0 mol % based on hydroxyethylpyrrolidone) of solid lithium hydroxide was added, the vacuum was established (300 mbar) and the suspension was heated (the jacket temperature was adjusted to 120° C. by means of thermostating). After approx. 10 minutes, the suspension began to boil; this time was selected as the start point (t=0 min). During the reaction, distillate (azeotrope of MMA and methanol) was removed continuously. After 300 min, the reaction was ended and the vacuum was broken. The suspension was cooled and then filtered through a pressure suction filter. 494 g of crude product were obtained.

Subsequently, 200 ppm of Kerobit® BPD (BASF Aktiengesellschaft, N,N'-di-sec-butyl-p-phenylenediamine) were added to 247 g of the crude product for stabilization. The mixture was distilled under reduced pressure, which first removed excess methyl methacrylate, and then the product of value was obtained (131-132° C. at 1.3 mbar). During the distillation, oxygen was injected into the mixture to be distilled.

133.5 g (90% yield) of product were obtained with the following composition (GC analysis): 97.8% N-(2-hydroxyethyl)pyrrolidone methacrylate, 0.6% hydroxyethylpyrrolidone, 0.2% methyl methacrylate and 1.4% other by-products. The APHA color number was 67.6 g of residue remained in the bottom.

Example 2

Preparation of N-(2-hydroxyethyl)pyrrolidone methacrylate with sodium hydroxide as the catalyst with subsequent purifying distillation Example 1 was reworked analogously, except that 1.2 g (30 mmol; 2.0 mol % based on hydroxyethylimidazole) of solid sodium hydroxide were used as the catalyst instead of lithium hydroxide. The reaction was ended after 120 min and the vacuum was broken. The suspension was cooled and then filtered through a pressure suction filter. 644 g of crude product were obtained.

Subsequently, 200 ppm of Kerobit® BPD (BASF Aktiengesellschaft, N,N'-di-sec-butyl-p-phenylenediamine) were added to the crude product for stabilization. The mixture was distilled under reduced pressure, which first removed excess methyl methacrylate, and then the product of value was obtained (142-144° C. at 2.8 mbar). During the distillation, oxygen was injected into the mixture to be distilled.

258 g (87% yield) of product were obtained with the following composition (GC analysis): 95.5% N-(2-hydroxyethyl)pyrrolidone methacrylate, 0.6% hydroxyethylpyrrolidone, 0.1% methyl methacrylate and 1.4% other by-products. The APHA color number was 50. 14 g of residue remained in the bottom.

Example 3

Preparation of N-(2-hydroxyethyl)pyrroldione methacrylate with potassium hydroxide as the catalyst with subsequent purifying distillation Example 1 was reworked analogously, except that 1.68 g (30 mmol; 2.0 mol % based on hydroxyethylimidazole) of solid potassium hydroxide were used as the catalyst instead of lithium hydroxide. The reaction was ended after 120 min and the vacuum was broken. The suspension was cooled and then filtered through a pressure suction filter. 636 g of crude product were obtained.

Subsequently, 200 ppm of Kerobit® BPD (BASF Aktiengesellschaft, N,N'-di-sec-butyl-p-phenylenediamine) were added to the crude product for stabilization. The mixture was distilled under reduced pressure, which first removed excess methyl methacrylate, and then the product of value was obtained (156-158° C. at 5.5 mbar). During the distillation, oxygen was injected into the mixture to be distilled.

258 g (79% yield) of product were obtained with the following composition (GC analysis): 98.5% N-(2-hydroxyethyl)pyrrolidone methacrylate, 0.5% hydroxyethylpyrrolidone and 1.4% other by-products. Methyl methacrylate was no longer present. The APHA color number was 58. 45 g of residue remained in the bottom.

Example 4

Preparation of N-(2-hydroxyethyl)pyrrolidone methacrylate with lithium hydroxide as the catalyst without phenothiazine as the stabilizer and without subsequent purifying distillation The apparatus described in Example 1 was initially charged with 280 mg of hydroquinone monomethyl ether (350 ppm), 600 g (6.0 mol) of methyl methacrylate (MMA) and 194 g (1.5 mol) of hydroxyethylpyrrolidone, which were stirred. Subsequently, 1.08 g (45 mmol; 3.0 mol % based on hydroxyethylpyrrolidone) of solid lithium hydroxide were added, the vacuum was established (300 mbar) and the suspension was heated (the jacket temperature was adjusted to 120° C. by means of thermostating). After approx. 10 minutes, the suspension began to boil; this time was selected as the start point (t=0 min). During the reaction, distillate (azeotrope of MMA and methanol) was removed continuously. After 180 min, the temperature in the bottom was adjusted to 60° C. and excess MMA was removed under reduced pressure. Subsequently, the vacuum was broken, and the suspension was cooled and then filtered through a pressure suction filter. 287 g of crude product (yield 97%) were obtained as a slightly yellowish liquid with the following composition (GC analysis): 96.5% N-(2-hydroxyethyl)pyrrolidone methacrylate, 0.4% hydroxyethylpyrrolidone, 0.7% methyl methacrylate and 2.3% other by-products. The APHA color number was 125.

Example 5

Preparation of N-(2-hydroxyethyl)pyrrolidone methacrylate with potassium hydroxide as the catalyst without hydroquinone monomethyl ether and phenothiazine as stabilizers and without subsequent purifying distillation The apparatus described in Example 1 was initially charged with 308 g (3.1 mol) of methyl methacrylate (MMA) which has been stabilized with 15 ppm of hydroquinone monomethyl ether, and 100 g (0.77 mol) of hydroxyethylpyrrolidone (APHA color number 118), which were stirred. Subsequently, 0.86 g (15 mmol; 2.0 mol % based on hydroxyethylpyrrolidone) of solid potassium hydroxide was added, the vacuum was established (300 mbar) and the suspension was heated (the jacket temperature was adjusted to 120° C. by means of thermostating). After approx. 10 minutes, the suspension began to boil; this time was selected as the start point (t=0 min). During the reaction, distillate (azeotrope of MMA and methanol) was removed continuously. After 150 min, the temperature in the bottom was adjusted to 60° C. and excess MMA was removed under reduced pressure. Subsequently, the vacuum was broken, and the suspension was cooled and then filtered through a pressure suction filter. 143 g of crude product (yield 94%) were obtained as a slightly yellowish liquid with the following composition (GC analysis): 95.3% N-(2-hydroxyethyl)pyrrolidone methacrylate, 1.1% hydroxyethylpyrrolidone, 1.7% methyl methacrylate and 2.0% other by-products. The APHA color number was 92.

Example 6

Preparation of N-(2-hydroxyethyl)pyrrolidone methacrylate with sodium acetylacetonate as the catalyst with subsequent purifying distillation Example 1 was reworked analogously, except that 4.2 g (30 mmol; 2.0 mol % based on hydroxyethylimidazole) of solid sodium acetylacetonate were used as the catalyst instead of lithium hydroxide. The reaction was ended after 180 min and the vacuum was broken. The suspension was cooled and then filtered through a pressure suction filter. 457 g of crude product were obtained.

Subsequently, 200 ppm of Kerobit® BPD (BASF Aktiengesellschaft, N,N'-di-sec-butyl-p-phenylenediamine) were added to 448 g of the crude product for stabilization. The mixture was distilled under reduced pressure, which first removed excess methyl methacrylate, and then the product of value was obtained in two fractions (148-149° C. at 4 mbar). During the distillation, oxygen was injected into the mixture to be distilled. 39 g of residue remained in the bottom.

229 g (79% yield) of product were obtained with the following composition (GC analysis) and color number:

| Fraction | Product[1] [%] | HEP[2] [%] | MMA [%] | By-products[3] [%] | Color number [APHA] |
|---|---|---|---|---|---|
| 1 (183 g) | 95.1 | 2.7 | 0.5 | 1.7 | 63 |
| 2 (46 g) | 92.8 | 3.5 | 0.5 | 3.2 | 79 |

[1]N-(2-Hydroxyethyl)pyrrolidone methacrylate
[2]Hydroxyethylpyrrolidone
[3]Sum of the other by-products

The invention claimed is:

1. A process for preparing a (meth)acrylic ester (F) of an N-hydroxyalkylated lactam, comprising:
   esterifying a cyclic N-hydroxalkylated lactam with (meth)acrylic acid (S) or transesterifing a cyclic N-hydroxalkylated lactam with a (meth)acrylic ester (D), in either case in the presence of a catalyst (K),
   wherein the cyclic N-hydroxyalkylated lactam (L) is of formula:

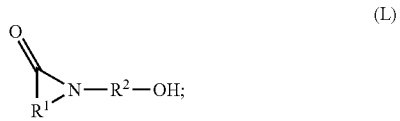

wherein $R^1$ is an uninterrupted $C_1$-$C_5$-alkylene or a $C_2$-$C_{20}$-alkylene interrupted by at least one selected from the group consisting of an oxygen atom, a sulfur atom, an optionally substituted imino group, a cycloalkyl group, —(CO)—, —O(CO)O—, —(NH)(CO)O—, —O(CO)(NH)—, —O(CO)—, and —(CO)O—;
   wherein $R^1$ is optionally substituted by at least one selected from the group consisting of an aryl group, an alkyl group, an aryloxy group, an alkyloxy group, a heteroatom, and a heterocycle;
   with the proviso that an atom of $R^1$ directly adjacent to the lactam carbonyl group is a carbon atom;
   wherein either
   (I) $R^2$ is an uninterrupted $C_1$-$C_{20}$-alkylene group, an uninterrupted $C_5$-$C_{12}$-cycloalkylene group, an uninterrupted $C_6$-$C_{12}$-arylene group, or a $C_2$-$C_{20}$-alkylene interrupted by at least one selected from the group consisting of an oxygen atom, a sulfur atom, an optionally substituted imino group, a cycloalkyl group, —(CO)—, —O(CO)O—, —(NH)(CO)O—, —O(CO)(NH)—, —O(CO)—, and —(CO)O— and
   $R^2$ is optionally substituted by at least one selected from the group consisting of an aryl group, an alkyl group, an aryloxy group, an alkyloxy group, a heteroatom, and a heterocycle,
   or
   (II) $R^2$—OH is a group of formula —$[X_i]_k$—H,
   k is from 1 to 50 and
   each $X_i$ is independently selected from the group consisting of —$CH_2$—$CH_2$—O—, —$CH_2$—$CH_2$—N(H)—, —$CH_2$—$CH_2$—$CH_2$—N(H)—, —$CH_2$—$CH(NH_2)$—, —$CH_2$—$CH(NHCHO)$—, —$CH_2$—$CH(CH_3)$—O—, —$CH(CH_3)$—$CH_2$—O—, —$CH_2$—$C(CH_3)_2$—O—, —$C(CH_3)_2$—$CH_2$—O—, —$CH_2$—$CH_2$—$CH_2$—O—, —$CH_2$—$CH_2$—$CH_2$—$CH_2$—O—, —$CH_2$—CHVin-O—, —CHVin-$CH_2$—O—, —$CH_2$—CHPh-O—, and —CHPh-$CH_2$—O—,
   wherein Ph is phenyl, and
   Vin is vinyl;
   and wherein the catalyst (K) is an alkali metal hydroxide, an alkaline earth metal hydroxide, a metal acetylacetonate, or any combination thereof.

2. The process of claim 1, wherein the catalyst (K) is lithium hydroxide, sodium hydroxide, potassium hydroxide, magnesium hydroxide, calcium hydroxide, or any combination thereof.

3. The process of claim 2, wherein the catalyst (K) is lithium hydroxide, sodium hydroxide, potassium hydroxide, or any combination thereof.

4. The process of claim 1, wherein the catalyst (K) is lithium hydroxide, sodium hydroxide, potassium hydroxide, or any combination thereof.

5. The process of claim 1,
   wherein the catalyst (K) is an acetylacetonate of a transition metal, an alkali metal, an alkaline earth metal, aluminum, or any combination thereof.

6. The process of claim 1, wherein the catalyst (K) is lithium acetylacetonate (Li(acac)), sodium acetylacetonate (Na(acac)), potassium acetylacetonate (K(acac)), calcium acetylacetonate (Ca(acac)$_2$), or any mixture thereof, and
   wherein (acac) is an acetylacetonate ion.

7. The process according to claim 1, wherein $R^1$ is selected from the group consisting of 1,2-ethylene, 1,2-propylene, 1,1-dimethyl-1,2-ethylene, 1-hydroxymethyl-1,2-ethylene, 2-hydroxy-1,3-propylene, 1,3-propylene, 1,4-butylene, 1,5-pentylene, 2-methyl-1,3-propylene, 2-ethyl-1,3-propylene, 2,2-dimethyl-1,3-propylene and 2,2-dimethyl-1,4-butylene.

8. The process according to claim 1, wherein $R^2$ is selected from the group consisting of 1,2-ethylene, 1,2-propylene, 1,1-dimethyl-1,2-ethylene, 1-hydroxymethyl-1,2-ethylene, 2-hydroxy-1,3-propylene, 1,3-propylene, 1,4-butylene, 1,6-hexylene, 2-methyl-1,3-propylene, 2-ethyl-1,3-propylene, 2,2-dimethyl-1,3-propylene, 2,2-dimethyl-1,4-butylene, 1,2-cyclopentylene, 1,3-cyclopentylene, 1,2-cyclohexylene, 1,3-cyclohexylene, ortho-phenylene, 3-oxa-1,5-pentylene, 3,6-dioxa-1,8-octylene and 3,6,8-trioxa-1,8,11-undecylene.

9. The process according to claim 1, wherein (L) is selected from the group consisting of N-(2-hydroxyethyl)pyrrolidone, N-(2-hydroxypropyl)pyrrolidone, N-(2'-(2-hydroxyethoxy)ethyl)pyrrolidone, N-(2-hydroxyethyl)caprolactam, N-(2-hydroxypropyl)caprolactam and N-(2'-(2-hydroxyethoxy)ethyl)caprolactam.

10. The process according to claim 1, wherein the esterifying or transesterifying comprises continuously introducing an oxygenous gas into the N-hydroxalkylated lactam (L) and the (meth)acrylic acid (S) or (meth)acrylic ester (D).

11. A process for making a dispersion, comprising:
   esterifying a cyclic N-hydroxalkylated lactam or transesterifing a cyclic N-hydroxalkylated lactam, in either case by the process of claim 1, to obtain a (meth)acrylic ester, and
   reacting the (meth)acrylic ester as a monomer or comonomer to obtain a dispersion material, and
   dispersing the dispersion material.

* * * * *